United States Patent [19]

Tanaka et al.

[11] Patent Number: 4,677,191

[45] Date of Patent: Jun. 30, 1987

[54] COPOLYMER AND METHOD FOR PRODUCING THE SAME

[75] Inventors: Motoaki Tanaka, Urawa; Yasuaki Ogawa, Ibaraki; Tsutomu Miyagawa; Toshio Watanabe, both of Kawagoe, all of Japan

[73] Assignees: Wada Pure Chemical Ind., Ltd.; Takeda Chemical Industries, Ltd., both of Higashi, Japan

[21] Appl. No.: 751,672

[22] Filed: Jul. 3, 1985

[30] Foreign Application Priority Data

Jul. 6, 1984 [JP] Japan .................................. 59-140356

[51] Int. Cl.$^4$ ............................................. C08G 63/06
[52] U.S. Cl. ..................................... 528/361; 528/354
[58] Field of Search ................. 528/354, 355, 357, 361

[56] References Cited

U.S. PATENT DOCUMENTS

| | | |
|---|---|---|
| 1,995,970 | 3/1935 | Dorough ............................... 528/361 |
| 2,362,511 | 11/1939 | Teeters et al. ....................... 528/361 |
| 2,438,208 | 3/1948 | Filachione et al. ................. 528/361 |
| 2,703,316 | 3/1955 | Schneider ............................ 528/354 |
| 2,758,987 | 8/1956 | Salzberg ........................... 528/361 X |
| 3,636,956 | 1/1972 | Schneider ........................ 528/354 X |
| 3,839,297 | 10/1974 | Wasserman et al. ........... 528/354 X |
| 4,137,921 | 2/1979 | Okuzumi et al. ............... 528/354 X |
| 4,273,920 | 6/1981 | Nevin .................................. 528/361 |

FOREIGN PATENT DOCUMENTS 0058481 8/1982 European Pat. Off. .

OTHER PUBLICATIONS

Asahara et al., "Production of Polyglycolide.Lactide and Properties of the Product", J. Chem. Soc. Japan, 65 (1965), No. 5, pp. 983-986.

*Primary Examiner*—Earl Nielsen
*Attorney, Agent, or Firm*—Wegner & Bretschneider

[57] ABSTRACT

A copolymer of lactic acid and glycolic acid which has a weight-average molecular weight of not less than about 5000 and a dispersity of about 1.5 to 2 is advantageously used as a biodegradable polymer for medical preparation.

12 Claims, No Drawings

COPOLYMER AND METHOD FOR PRODUCING THE SAME

The present invention relates to a copolymer of lactic acid and glycolic acid, and a method for producing the copolymer in the absence of a catalyst.

In recent years, degradable polymers have attracted a good deal of attention, for example, as a readily degradable polymer serving to mitigate environmental pollution by plastics and also as a biodegradable polymer for medical uses.

As the method for producing a copolymer of lactic acid and glycolic acid, there is mentioned a method disclosed in U.S. Pat. No. 4,273,920. In said U.S. Patent, it is stated that the copolymer being substantially free of polymerization catalyst is obtained by reacting lactic acid with glycolic acid in the presence of a readily removable strong acid ion-exchange resin, and removing the resin therefrom.

However, the copolymers produced by the above-described method all exhibit a dispersity in molecular weight as high as nearly 3 or more and in use cause a great complexity in factors involved in solubility and other aspects, thus causing major problems in controlling such factors. Therefore, they cannot be said to be very useful, when they are used, for example, as a biodegradable polymer for medical use. In addition, this method allows the strong acid ion-exchange resin being used as a polymerization catalyst to deteriorate due to heat during a polycondensation reaction under heating and to become dissolved in the resulting copolymer, thereby contributing to the development of coloration of the copolymer. Once the copolymer becomes colored, it is difficult to eliminate such coloration, and it is practically impossible to remove completely such coloration, the coloration shows that the catalyst, i.e. strong acid ion-exchange resin, cannot be completely removed. It goes without saying that such coloration not only diminishes the value as an article of commerce but also is in the undesirable state, because it is attributed to impurities.

The present inventors conducted intensive research on the method for producing a copolymer of lactic acid and glycolic acid, which is effective and free from the above-mentioned disadvantages, and have found that the desired copolymer of lactic acid and glycolic acid is obtained by a polycondensation of these compounds in the absence of a catalyst. The present inventors conducted further research and have completed the present invention.

The present invention is directed to:
(1) a copolymer of lactic acid and glycolic acid, which has a weight-average molecular weight of about 5,000 to 30,000 and a dispersity of about 1.5 to 2, and
(2) a method for producing a copolymer of lactic acid and glycolic acid, a copolymer having a weight-average molecular weight of not less than about 5,000 and a dispersity of about 1.5 to 2, which comprises subjecting lactic acid and glycolic acid or a low molecular polymer or copolymer of them to a polycondensation reaction under heating and reduced pressure in the absence of a catalyst.

In the method of the present invention, lactic acid and glycolic acid are employed, as the starting materials, in the form of crystals, powders or granules as such, or in the form of an aqueous solution. The concentration of the solution is arbitrarily selected, preferably as high as possible, and more preferably not lower than 85 % (w/w).

As the low molecular polymer of lactic acid or glycolic acid, there are mentioned an oligomer (e.g. dimer, trimer, etc.) of lactic acid, an oligomer (e.g. dimer, trimer, etc.) of glycolic acid and so on.

As the low molecular polymer or copolymer, employable in a present method as a starting material, of lactic acid and glycolic acid, there can serve those which are produced by subjecting lactic acid and/or glycolic acid to polycondensation reaction in the absence of a catalyst under for example about 100° to 150° C./350 to 30 mmHg for more than atout 2 hours, normally about 2 to 10 hours, more preferably while increasing the temperature and the degree of reduced pressure stepwise from about 105° C./350 mmHg to 150° C./30 mmHg for about 5 to 6 hours, to thereby remove water. In this process, the low molecular polymer or copolymer of molecular weight of about 2000 to 4000 is obtained.

Furthermore, as the low molecular copolymers, there are mentioned those which are obtainable by the methods described in Kogyo Kagaku Zasshi (Journal of the Chemical Society of Japan), vol. 68, pp. 983–986 (1965), i.e. lactic acid and glycolic acid are reacted at a normal atmospheric pressure and in the absence of a catalyst at 202° C. for 6 hours, or U.S. Pat. No. 2,362,511, i.e. lactic acid and glycolic acid are reacted at a temperature of 200° C. holding the mixture at that temperature for a period of about 2 hours and subsequently continuing the heating for another period of about ½ hour under vacuum.

The ratio of lactic acid to glycolic acid in the present copolymer is preferably about 50 to 95 weight % of lactic acid and 50 to 5 weight % of glycolic acid, preferably about 60 to 95 weight % of lactic acid and about 40 to 5 weight % of glycolic acid, still more preferably about 60 to 85 weight % of lactic acid and about 40 to 15 weight % of glycolic acid. The ratio is especially preferably about 75±2 mol % of lactic acid and about 25±2 mol % of glycolic acid.

In the present method, a solvent may be employed, especially starting materials are both crystals, powders or granules. As the solvent, there are mentioned, for example water, methanol, ethanol, acetone, etc.

The present method is carried out under heating and reduced pressure in the absence of a catalyst. The heating is carried out by heating the reaction system at about 150° to 250° C., preferably about 150° to 200° C. The reduced pressure is normally about 30 to 1 mmHg, preferably about 10 to 1 mmHg. The reaction time of the present polycondensation reaction is normally not less than about 10 hours, preferably about 10 to 150 hours, more preferably about 10 to 100 hours.

Referring to the reaction steps and conditions in the present method when lactic acid and glycolic acid are employed as the starting materials, the following are preferred: A heating reaction under reduced pressure may be allowed to proceed at about 100° to 150° C./350 to 30 mmHg for not less than about 2 hours, normally about 2 to 10 hours, for example, for about 5 to 6 hours while increasing the temperature and the degree of reduced pressure stepwise to about 105° C./350 mmHg to 150° C./30 mmHg, to thereby remove water, followed by a dehydration polycondensation reaction at about 150° to 220° C./10 to 1 mmHg for not less than about 10 hours; and normally up to about 100 hours may be adequate.

When a low molecular polymer or copolymer is employed as the starting material, preferable reaction conditions are as follows: A dehydration polycondensation reaction is carried out at about 150° to 200° C./10 to 1 mmHg for not less than 10 hours; and normally up to about 100 hours may be adequate.

After the termination of the reaction, the desired copolymer can be readily obtained by eliminating insolubles through mere hot filtration of the reaction solution or filtration after dissolution of the copolymer in a suitable solvent such as methylene chloride, dichloroethane, chloroform, acetone in an amount of equal to about 10-times that of the copolymer, whereupon no subsequent treatment is required to be carried out in the former case where the reaction solution is filtered as such and the employed solvent is concentrated or distilled off in the latter case where the reaction solution is filtered after being dissolved in a solvent. If desired, separation may be performed in accordance with a conventional method, for example, by pouring the filtered reaction solution, either directly or in the form of a concentrated filtrate in the case of a solvent being used, into a large amount of a precipitant, and if further required, purification may be carried out by reprecipitation, etc.

According to the present invention, there can be formed a copolymer consisting of lactic acid and glycolic acid units having a weight-average molecular weight of not less than about 5,000, preferably about 5,000 to 30,000, and the resulting copolymer has a dispersity of about 1.5 to 2.

As the copolymer obtained by the present method has a low degree of dispersity, the distribution of molecular weight of the copolymer is not wide.

Furthermore, in the present method, as no catalyst is used, the product is produced by polycondensation reaction in the absence of a catalyst, and is free of coloration.

The copolymer obtained by the present method can be utilized mainly as a base for drug preparation. For example, the copolymer can be advantageously utilized by incorporating steroid hormones, peptide hormones or anti-tumor agents, etc. into it to process into an embedded type or microcapsule type of controlled release preparations or by preparing fine particles containing an anti-tumor agent to process into a therapeutic agent for embolization.

The Experiment Examples and Examples are described below to illustrate the present invention in more detail.

Experiment Example 1

After 160 g (1.5 mol) of a 85% aqueous solution of lactic acid and 38 g (0.5 mol) of glycolic acid were mixed and heated under reduced pressure and under a nitrogen gas stream under the stepwise varying conditions of 100° to 150° C./350 to 30 mmHg for 6 hours to remove the resulting water, the mixture was subjected to a dehydration polycondensation reaction at 175° C./5 mmHg for 72 hours.

Shown in Table 1 is the relationship between reaction time and weight-average molecular weight attained in the production of copolymer of lactic acid and glycolic acid and its dispersity in accordance with the present process.

Also shown in Table 1 for the purpose of comparison are the results obtained with Dowex 50 (a cross-linked polystyrene resin, Dow Chemical Co., U.S.A.), a strongly acidic ion-exchange resin being commercially available, which was used as a polymerization catalyst.

TABLE 1

Comparison between the present process and process utilizing ion exchange resin in terms of molecular weight attained and its dispersity

| Reaction time | The present method | | Control example (Dowex 50 used as a catalyst) | |
| --- | --- | --- | --- | --- |
| | Weight-average mol. weight | Dispersity | Weight-average mol. weight | Dispersity |
| 12 hours | 5,200 | 1.70 | — | — |
| 24 hours | 9,600 | 1.68 | 9,100 | 2.43 |
| 36 hours | 13,500 | 1.71 | 11,400 | 2.63 |
| 48 hours | 15,800 | 1.66 | 14,900 | 2.80 |
| 60 hours | 18,000 | 1.71 | 17,800 | 2.81 |
| 72 hours | 20,700 | 1.66 | 20,200 | 2.80 |
| Appearance of the polymer* | White | | Dark brown (The color deepens with time) | |

Note:
*Each of the copolymers obtained after the respective reaction time was dissolved in methylene chloride of the volume four times that of the copolymer, and the solution was filtered and then concentrated to distill off the solvent; the resulting copolymers were tested in accordance with JIS K8004-2 (namely, about 3 g of the test specimen is taken and examined on a sheet of white paper).

The weight-average molecular weight and dispersity $$\left( \text{dispersity} = \frac{\text{weight} - \text{average molecular weight}}{\text{number} - \text{average molecular weight}} \right)$$

in the present specification were measured by gel permeation chromatography utilizing the standard polystyrene with the known molecular weight.

As is clear from Table 1, the present invention can permit readily the production of high-molecular-weight lactic acid glycolic acid copolymers having a weight-average molecular weight of not less than about 5,000; the resulting copolymers hardly exhibit color and show a dispersity of not more than 2.

Furthermore, analysis of nuclear magnetic resonance spectrometry on the resulting copolymer obtained in the above in a $CDCl_3$ solution indicates the following composition of lactic acid and glycolic acid.

| Copolymer ratio of the present copolymer | | |
| --- | --- | --- |
| | Copolymer ratio mol % (weight %) | |
| Reaction time | lactic acid | glycolic acid |
| 12 hours | 75.5 | 24.5 |
| | (79.3) | (20.7) |
| 24 hours | 75.5 | 24.5 |
| | (79.3) | (20.7) |
| 36 hours | 75 | 25 |
| | (78.8) | (21.2) |
| 48 hours | 75.5 | 24.5 |
| | (79.3) | (20.7) |
| 60 hours | 76 | 24 |
| | (79.7) | (20.3) |
| 72 hours | 75.5 | 24.5 |
| | (79.3) | (20.7) |

EXAMPLE 1

Weighed in a four-necked flask fitted with a thermometer, condenser and inlet tube for nitrogen gas were 191 g of a 85% aqueous solution of lactic acid and 17.5 g of glycolic acid, and heating under reduced pressure was carried out, under a stream of nitrogen gas, at the internal temperature and internal pressure of 105° C. and 350 mmHg to 150° C. and 30 mmHg over the period of 6 hours to remove the resulting water. Successively, heating was conducted under reduced pressure of 3 mmHg at the internal temperature of 175° C. for 72 hours. The reaction solution was cooled to room temperature to give 140 g of an almost colorless bulk copolymer as a copolymer of lactic acid and glycolic acid. The copolymer showed a weight-average molecular weight of 22,000, a dispersity of 1.70 and a composition of lactic acid and glycolic acid of 89 mol %:11 mol % (90.9 weight %:9.1 weight %).

EXPERIMENT EXAMPLE 2

To 191 g of a 85% aqueous solution of lactic acid and 17.5 g of glycolic acid was added 6.8 g of Dowex 50W, and in the manner of Example 1, heating under reduced pressure was conducted, under a stream of nitrogen gas, at the internal temperature and internal pressure of 105° C. and 350 mmHg to 150° C. and 30 mmHg, respectively, over the period of 6 hours to remove the resulting water. Furthermore, 6.8 g of Dowex 50W was additionally added, and heating was carried out under reduced pressure of 3 mmHg at the internal temperature of 175° C. for 72 hours. The reaction solution was filtered hot to remove the Dowex 50W, and the filtrate was cooled to room temperature to give 131 g of a bulk copolymer with a weight-average molecular weight of 23,700 and a dispersity of 2.88, which was brown colored. The resulting copolymer showed a composition of lactic acid and glycolic acid of 88.5 mol % :11.5 mol % (90.5 weight %:9.5 weight %).

EXAMPLE 2

Placed in the same polymerization apparatus as used in Example 1 were 106 g of a 85% aqueous solution of lactic acid and 76 g of glycolic acid, and heating under reduced pressure was carried out, under a stream of nitrogen gas, at the internal temperature and internal pressure of 105° C. and 350 mmHg to 150° C. and 30 mmHg, stepwise, over the period of 3 hours and then the resulting water was removed. Successively, heating was conducted under reduced pressure of 3 mmHg at the internal temperature of 180° C. for 36 hours, and the reaction solution was cooled to room temperature to give 124 g of an almost colorless bulk polymer as a copolymer from lactic acid and glycolic acid. The copolymer showed a weight-average molecular weight of 15,300, a dispersity of 1.73, and a composition of lactic acid and glycolic acid of 50.5 mol %:49.5 mol % (55.9 weight % :44.1 weight %).

EXAMPLE 3

146 g of a 93% aqueous solution of lactic acid and 38 g of glycolic acid was used, a heating reaction was conducted at the temperature of 202° C. for 6 hours, whereby a copolymer with a weight-average molecular weight of 2,700 and a composition of lactic acid and glycolic acid of 75 mol %:25 mol % was obtained. Weighed in the same polymerization apparatus as used in Example 1 was 100 g of this copolymer, and heating was carried out under reduced pressure of 5 mmHg at the internal temperature of 175° C. for 70 hours, and the reaction solution was cooled to room temperature to give 92 g of an almost colorless bulk copolymer with a weight-average molecular weight of 17,700 and a dispersity of 1.85. The resulting copolymer showed a composition of lactic acid and glycolic acid of 75.5 mol % : 24.5 mol % (79.3 weight %:20.7 weight %).

EXAMPLE 4

Placed in the same polymerization apparatus as used in Example 1 were 97 g of lactic acid dimer (Lactic acid lactate) and 54 g of glycolic acid dimer (Glycologlycolic acid), and heating was carried out under reduced pressure of 5 mmHg at internal temperature of 180° C. for 48 hours. The reaction solution was cooled to room temperature to give 105 g of an almost colorless bulk copolymer with a weight-average molecular weight of 18,300 and a dispersity of 1.76. The copolymer showed a composition of lactic acid and glycolic acid of 60 mol %:40 mol %(65.1 weight %:34.9 weight %).

EXAMPLE 5

After 3337 g (33 mol) of a 89% aqueous solution of lactic acid and 836 g (11 mol) of glycolic acid were mixed and heated under reduced pressure and under a nitrogen gas stream under the stepwise varying conditions of 100° to 150° C./350 to 30 mmHg for 6 hours to remove the resulting water, the mixture was subjected to a dehydration polycondensation reaction at 175° C./5 mmHg for 50 hours. The reaction solution was cooled to room temperature to give 2400 g of an almost colorless bulk copolymer with a weight-average molecular weight of 14400 and a dispersity of 1.66. The copolymer showed a composition of lactic acid and glycolic acid of 75 mol %:25 mol % (78.8 weight %:21.2 weight %).

What we claim is:

1. A copolymer of lactic acid and glycolic acid free from catalyst, which has a weight-average molecular weight of about 5,000 to 30,000 and a dispersity of about 1.5 to 2.

2. A copopymer as claimed in claim 1, wherein the copolymer ratio is about 50 to 95 weight % of lactic acid and about 50 to 5 weight % of glycolic acid.

3. A copolymer as claimed in claim 1, wherein the copolymer ratio is about 60 to 95 weight % of lactic acid and about 40 to 5 weight % of glycolic acid.

4. A copolymer as claimed in claim 1, wherein the copolymer ratio is about 60 to 85 weight % of lactic acid and about 40 to 15 weight % of glycolic acid.

5. A copolymer as claimed in claim 1, wherein the copolymer ratio is about 75±2 mol % of lactic acid and about 25±2 mol % of glycolic acid.

6. A method for producing a copolymer of lactic acid and glycolic acid, the copolymer having a weight-average molecular weight of not less than about 5,000 and a dispersity of about 1.5 to 2, which comprises subjecting lactic acid and glycolic acid or a low molecular polymer or copolymer of them to a polycondensation reaction under heating and reduced pressure in the absence of a catalyst.

7. A method as claimed in claim 6, wherein the low molecular copolymer of lactic acid and glycolic acid is produced by subjecting lactic acid and glycolic acid to undergo a condensation reaction in the absence of a catalyst and remove water, and the polycondensation reaction is carried out for about not less than 10 hours.

8. A method as claimed in claim 6, wherein the weight-average molecular weight of the resulting copolymer is about 5,000 to 30,000.

9. A method as climed in claim 6, wherein the copolymer ratio is about 50 to 95 weight % of lactic acid and about 50 to 5 weight % of glycolic acid.

10. A method as claimed in claim 6, wherein the copolymer ratio is about 60 to 95 weight % of lactic acid and about 40 to 5 weight % of glycolic acid.

11. A method as claimed in claim 6, wherein the copolymer ratio is about 60 to 85 weight % of lactic acid and about 40 to 15 weight % of glycolic acid.

12. A method as claimed in claim 6, wherein the copolymer ratio is about 75±2 mol % of lactic acid and about 25±2 mol % of glycolic acid.

* * * * *

UNITED STATES PATENT AND TRADEMARK OFFICE
CERTIFICATE OF CORRECTION

PATENT NO. : 4,677,191
DATED : June 30, 1987
INVENTOR(S) : TANAKA et al

It is certified that error appears in the above-indentified patent and that said Letters Patent is hereby corrected as shown below:

ON THE TITLE PAGE

In the assignment section, delete "Wada" and insert --Wako--;

delete "Higashi" and insert --Osaka--.

Signed and Sealed this

Eighth Day of June, 1993

Attest:

MICHAEL K. KIRK

Attesting Officer

Acting Commissioner of Patents and Trademarks